United States Patent
Dulog et al.

[11] Patent Number: 6,106,818
[45] Date of Patent: Aug. 22, 2000

[54] METHOD FOR REMOVING DEAD SURFACE CELLS, DIRT, OIL, AND BLACKHEADS FROM THE SKIN AND RELATED COMPOSITIONS AND ARTICLES

[75] Inventors: Reilly Canay Dulog, Edison; James Joseph Ferone, Bridgewater; Beverly Ann Reisinger, East Brunswick; Patricia Beatrice Siuta, Mahwah, all of N.J.

[73] Assignee: Revlon Consumer Products Corporation, New York, N.Y.

[21] Appl. No.: 09/143,609

[22] Filed: Aug. 31, 1998

Related U.S. Application Data

[60] Provisional application No. 60/083,124, Apr. 27, 1998.

[51] Int. Cl.[7] .............................. A61K 31/74; A61K 7/48
[52] U.S. Cl. ..................... 424/78.03; 424/401; 424/402; 424/443; 514/859
[58] Field of Search ..................... 424/401, 402, 424/443, 78.03; 514/859

[56] References Cited

U.S. PATENT DOCUMENTS

| | | | |
|---|---|---|---|
| D. 388,533 | 12/1997 | Uemura | D28/4 |
| D. 388,534 | 12/1997 | Uemura | D28/4 |
| 3,683,091 | 8/1972 | Nagata | 424/331 |
| 3,966,902 | 6/1976 | Chromacek | 424/59 |
| 4,126,142 | 11/1978 | Saute | 132/7 |
| 4,163,092 | 7/1979 | Steckler | 526/292 |
| 4,532,937 | 8/1985 | Miller . | |
| 4,581,402 | 4/1986 | Dunk | 524/317 |
| 4,619,829 | 10/1986 | Motschan | 424/128 |
| 4,629,623 | 12/1986 | Balazs | 424/78 |
| 4,879,361 | 11/1989 | Rehmer | 526/201 |
| 4,891,228 | 1/1990 | Thaman et al. . | |
| 4,990,339 | 2/1991 | Scholl | 424/443 |
| 5,026,552 | 6/1991 | Gueret | 424/401 |
| 5,084,270 | 1/1992 | Ciaudelli . | |
| 5,208,016 | 5/1993 | Ohmae | 424/78.27 |
| 5,254,338 | 10/1993 | Sakai | 424/78.35 |
| 5,449,519 | 9/1995 | Wolf et al. . | |
| 5,512,277 | 4/1996 | Uemura | 424/78.03 |
| 5,620,694 | 4/1997 | Girardot . | |
| 5,723,138 | 3/1998 | Bae | 424/401 |
| 5,744,149 | 4/1998 | Girardot . | |
| 5,879,693 | 3/1999 | Wolfe . | |

FOREIGN PATENT DOCUMENTS

| | | |
|---|---|---|
| 0 327 327 | 1/1994 | European Pat. Off. . |
| 9-216808 | 9/1997 | Japan . |
| WO 96/14822 | 5/1996 | WIPO . |
| WO 97/28786 | 8/1997 | WIPO . |
| WO 97/32567 | 9/1997 | WIPO . |

*Primary Examiner*—Thurman K. Page
*Assistant Examiner*—Brian K. Seidleck
*Attorney, Agent, or Firm*—Julie Blackburn

[57] ABSTRACT

A method for removing dead surface cells, dirt, oil, or blackheads from the skin, and preventing or ameliorating the effects of blemishes or acne vulgaris, comprising applying to the skin a laminate comprised of a fabric strip and a solvent activated composition containing at least one nonionic polymer in combination with at least one skin conditioning agent, leaving the laminate on the skin until the solvent has substantially evaporated, and peeling the laminate off the skin, thereby removing dead surface cells, dirt, oil, or blackheads from the skin; as well as related articles and compositions.

18 Claims, 2 Drawing Sheets

METHOD FOR REMOVING DEAD SURFACE CELLS, DIRT, OIL, AND BLACKHEADS FROM THE SKIN AND RELATED COMPOSITIONS AND ARTICLES

RELATED APPLICATIONS

This application is a continuation-in-part of provisional patent application Ser. No. 60/083,124, filed Apr. 27, 1998.

TECHNICAL FIELD

The invention is in the field of cleaning skin by removing dead surface cells, dirt, oil, and blackheads (also referred to as keratotic plugs) and alleviating the effects of acne vulgaris and blemishes by applying to the skin a fabric strip having layered thereon a skin cleaning composition, and removing the strip from the skin after an appropriate period of time; as well as the related compositions and articles.

BACKGROUND OF THE INVENTION

A variety of methods and articles are known for cleaning the skin above and beyond normal daily cleansing. For example, face masks are taught in U.S. Pat. No. 5,139,711 to Gerstein. This mask is a composition containing hydrolyzed grain endproducts, seaweed derivatives, and water. The composition is applied to the skin and allowed to dry for an appropriate period of time. The composition is then rinsed off with water. This rinse away mask deep cleans the skin and removes dead surface cells and other skin debris.

Another type of mask, referred to as a "peel away" mask is taught in U.S. Pat. No. 4,126,142, to Saute, where a paste of sodium polystyrene sulfonate is applied to the skin and allowed to dry to form a film. When the dried film is removed from the skin by peeling away, scurf skin and sebaceous soil is also removed. Rinse away and peel away masks have their disadvantages. In particular, some consumers believe that rinse away masks are not as effective in cleaning the skin because they are simply rinsed off the skin when dried. On the other hand, while peel away masks are believed to better cleanse skin and remove dead surface cells, it is often difficult to peel the mask away from the skin after it has dried. The dried film often rips as it is peeled away, or stubbornly clings to certain areas of the skin such as beneath earlobes and alongside the nose.

The problems with rinse away and peel away masks were addressed in U.S. Pat. No. 5,512,277, which teaches a method for removing keratotic plugs by layering a composition containing a salt forming polymer (i.e. an anionic, cationic, or amphoteric homopolymer or copolymer) onto a fabric patch made of rayon, nylon, and the like. The patch is applied to moistened skin for a certain period of time, then peeled away, leaving keratotic plugs and dead surface cells adhered to the removed patch. The pore strips described in U.S. Pat. No. 5,512,277 are effective in removing keratotic plugs and dead surface cells, the salt forming polymers used therein tend to irritate the skin as well as to unduly "strip" the skin surface cells. Over-stripped skin may be tender or raw, and very sensitive.

Accordingly, there is a need for a method and compositions for deep cleaning skin and removing dead surface cells, dirt, oil, and keratotic plugs or blackheads, without causing skin irritation or over stripping skin surface cells.

SUMMARY OF THE INVENTION

The invention comprises a method for removing dead surface cells, dirt, oil, or blackheads from the skin comprising the steps of:

(a) applying to the skin a laminate comprised of (i) a fabric strip, and (ii) a solvent activated composition containing at least one nonionic polymer in combination with at least one skin conditioning agent, composition side down, (b) leaving the laminate on the skin until the solvent has substantially evaporated, and (c) peeling the laminate off the skin, thereby removing dead surface cells, dirt, oil, or blackheads from the skin.

The invention also comprises a method for preventing or ameliorating the effects of acne vulgaris or blemishes comprising the steps of:

(a) applying to the skin a laminate comprised of (i) a fabric strip, and (ii) a solvent activated composition containing at least one nonionic polymer in combination with at least one skin conditioning agent, composition side down, (b) leaving the laminate on the skin until the solvent has substantially evaporated, and (c) peeling the laminate off the skin, thereby removing dead surface cells, dirt, oil, or blackheads from the skin.

The invention also comprises an article for removing dead surface cells, dirt, oil, or blackheads from the skin; and/or an article for treatment of acne vulgaris or blemishes, comprising, in combination:

a) a laminate comprised of (i) a fabric strip; and, layered onto said fabric strip, (ii) a solvent activatable composition comprised of at least one nonionic polymer and at least one skin conditioning agent; and b) a hermetically sealed package for enclosing said laminate.

The invention also comprises a skin cleaning composition comprising, by weight of the total composition:

(a) 1–95% of a nonionic polymer, and (b) 0.1–99% of an exfoliating agent selected from the group consisting of:

(i) alpha hydroxy acids (ii) alpha hydroxy acid esters (iii) beta hydroxy acids (iv) beta hydroxy acid esters (v) a beta hydroxy acid complexed to a carrier molecule (vi) N-alkoxyalkylamides, (vii) benzoic acid derivatives of the formula:

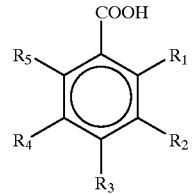

wherein $R_1$ is H, and $R_2$ through $R_5$ are each independently H, or OH with the proviso that there is at-least one OH radical present.

(viii) benzoyl peroxide, (ix) resorcinol; and (x) mixtures thereof.

BRIEF DESCRIPTION OF THE DRAWINGS

FIGS. 4a and 4b show suitable shapes for cleansing the nose. FIGS. 4c and 4d show examples of shapes suitable for cleansing the chin and cheek area.

DETAILED DESCRIPTION

Figure 1:
FIG. 1 illustrates the laminate of the invention which is a fabric strip having layered thereon a solvent activatable composition.

All percentages mentioned herein are percentages by weight unless otherwise indicated.

The term "solvent activated" means that the composition which is layered onto the fabric strip has been contacted with a solvent such as water, alcohol, or the like, which causes the composition to become moistened to a degree sufficient such that when the composition side of the laminate is pressed against the skin surface the laminate will adhere to the skin surface. This activation may occur by wetting the laminate, preferably the composition side of the laminate, with the solvent prior to applying it to the skin. In the alternative, the solvent activation may occur by wetting the skin itself with the solvent prior to applying the laminate, composition side down, to the wetted skin surface. Although it is preferred to activate the solvent activatable composition by contacting it with solvent as mentioned above, in some cases and in some environments, the skin surface itself, or the surrounding environment may be moist enough (i.e. the skin surface itself contains a sufficient level of water) that it is not necessary to add solvent to the laminate or the skin in order to cause activation.

The term "solvent activatable" means that the composition can be activated, or made to cause the fabric strip to adhere to the skin surface, by contacting it with a dermatologically safe solvent such as water.

The term "dermatologically safe solvent" means any aqueous or non-aqueous solvent that is generally recognized as safe for use in skin care products, including but not limited to water, ethyl alcohol, isopropyl alcohol, and the like. Preferably the solvent is water.

The Composition Used in the Method of the Invention

The solvent activatable composition used in the method of the invention comprises at least one nonionic polymer in combination with at least one skin conditioning agent. Preferably this composition comprises about 1–95%, preferably 3–85%, more preferably 10–69% of the nonionic polymer and 0.1–99%, preferably 0.5–95%, more preferably 1–90% of the skin conditioning agent. While the solvent activatable composition may be aqueous-based or anhydrous, preferably it is aqueous based, containing about 0.01–95%, preferably 0.1–90%, more preferably 0.5–85% by weight of the total composition of water. When the composition is first manufactured it is preferably in the aqueous form. The composition is then layered onto the fabric strip, or the release layer (as further discussed herein). If the latter, the fabric strip is then layered on top of the composition. The whole laminate is then allowed to dry. After drying, the water in the composition is substantially reduced, thereby leaving a substantially dried polymer composition within the laminate which may or may not contain very small levels of solvent in the composition, e.g. at or below about 30 weight percent, more preferably about 15 to 20 weight percent. When the polymer composition is substantially dried in the laminate it is referred to as "solvent activatable". When the polymer composition has absorbed an activating solvent such as water it is referred to as "solvent activated".

The Nonionic Polymer

The nonionic polymer used in the method of the invention is preferably formed by the addition polymerization of one or more ethylenically unsaturated monomers having substituent groups which impart a nonionic character to the polymer, meaning the polymer itself has no negative or positive charge. The polymer may be a homo- or copolymer, as well as a graft or block copolymer provided it is nonionic in character. Preferably the nonionic polymer is water soluble, and has a molecular weight ranging from about 5,000 to 5,000,000 daltons. Examples of suitable nonionic polymers are those made by polymerizing one or more monomers having the following general formula:

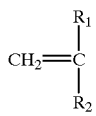

wherein:
R$_1$ is hydrogen; C$_{1-30}$ straight or branched chain alkyl; or halogen;
R$_2$ is hydrogen; halogen; hydroxyl; alkoxy; pyrrolidone; caprolactam; NXCYO wherein X and Y are each independently hydrogen, or a C$_{1-30}$ straight or branched chain alkyl; a substituted or unsubstituted aromatic, cyclic, alicyclic, or bicyclic ring where the substitutents are C$_{1-30}$ straight or branched chain alkyl or halogen; or COOM wherein M is a substituted or unsubstituted C$_{1-30}$ straight or branched chain alkyl where the substitutents are halogen or alkoxy; or OCOM wherein M is a substituted or unsubstituted C$_{1-30}$ straight or branched chain alkyl where the substituents are as identified above; pyrrolidone; caprolactam; or a substituted or unsubstituted aromatic, cyclic, alicyclic, or bicyclic ring where the substitutents are C$_{1-30}$ straight or branched chain alkyl or halogen.

The nonionic polymer used in the method of the invention may be a homopolymer or a copolymer of one or more of the above mentioned monomers, so long as the polymer itself is nonionic. Suitable copolymers include graft copolymers and block copolymers as well as interpolymers.

Preferably R$_1$ is hydrogen or methyl, more preferably hydrogen; and R$_2$ is hydroxyl; alkoxy; pyrrolidone; or NXCYO wherein X and Y are hydrogen. More preferably, R$_1$ is hydrogen and R$_2$ is hydroxyl; pyrrolidone; or NXCYO wherein X and Y are hydrogen. Examples of such polymers include polyvinyl alcohol (PVA), polyvinyl pyrrolidone (PVP), and poly(N-vinylformamide) (PVF). Particularly suitable for use in the method of the invention is PVP purchased from International Specialty Products under the tradename PVP K-120. In the preferred embodiment of the invention the polymer is formed by the polymerization of monomers containing amide groups, in particular, PVF. This material may be purchased from National Starch & Chemical, Bridgewater, N.J., in the form of a nonionic, water soluble fine white powder sold under the tradename Polymer 10174-02.

The Skin Conditioning Agent

The composition contains 0.1–99%, preferably 0.5–95%, more preferably 1–90% of the skin conditioning agent. A variety of skin conditioning agents are suitable, for example, they may fall into the general category of exfoliating agents, emollients, humectants, vitamins, and the like.

Exfoliating Agents

Preferably, the composition contains 0.01–20%, preferably 0.1–15%, more preferably 0.5–10% by weight of the total composition of an exfoliating agent. Examples of suitable exfoliating agents are:

1. Alpha Hydroxy Acids and Derivatives

Examples of suitable exfoliating agents include alpha hydroxy acids, or derivatives thereof. Suitable alpha hydroxy acids are disclosed in U.S. Pat. No. 5,091,171, which is hereby incorporated by reference. Such alpha hydroxy acids are organic carboxylic acids where one hydroxyl group is attached to the alpha carbon atom of the acid. The general structure of such alpha hydroxy acids may be represented by the following formula:

(Ra)(Rb)C(OH)COOH wherein Ra and Rb are H, F, Cl, Br, alkyl, aralkyl, or aryl group of saturated, unsaturated, straight or branched chain or cyclic form having 1–10 carbon atoms, and in addition Ra or Rb may carry one or more OH, CHO, COOH or alkoxy groups having 1 to 9 carbon atoms as well as mixtures of two or more different types of such groups.

2. Alpha Keto Acids and Derivatives.

Suitable alpha keto acids and derivatives are disclosed in U.S. Pat. No. 5,091,171, mentioned above. The general structure of such alpha keto acids may be represented by the formula below:

(Ra)COCOO(Rb)

wherein Ra and Rb are as set forth above.

The alpha hydroxy or alpha keto acids may exist in the ester form. Examples of such alpha hydroxy acids include glycolic acid, malic acid, pyruvic acid, mandelic acid, lactic acid, methyllactic acid, and so on. These alpha hydroxy acids may be esterified with, for example, a $C_{1-30}$ straight or branched chain alcohol, preferably a $C_{6-22}$ fatty alcohol. Examples of such compounds include isostearyl glycolate, isostearyl malate, isostearyl lactate, and the like.

2. Beta Hydroxy Acids and Derviatives

Also beta hydroxy acids such as salicylic acid, and derivatives thereof may be included in the compositions of the invention.

Examples of suitable beta hydroxy acids include salicylic acid or derivatives thereof. Derivatives of salicylic acid may be made by esterifying salicylic acid with a $C_{1-30}$, preferably $C_{6-22}$ straight or branched chain alcohol, or esterifying salicylic acid with a $C_{6-22}$ fatty acid. Preferred are derviatives of salicylic acid which are disclosed in U.S. Pat. No. 5,449,519, which is hereby incorporated by reference. Such derivatives comprise salicylic acid complexed to a carrier molecule which preferably contains a free amino or hydroxyl group. More preferably the salicylic acid is complexed with hydrolyzed vegetable protein.

3. N-Alkoxyalkylamides and Certain Diamides

Preferably, the composition contains one or more N-alkoxyalkylamides or diamides such as those disclosed in U.S. Pat. Nos. 5,084,270 and 5,139,784, which are hereby incorporated by reference. Examples of such alkoxyalkylamides are those having the general formula:

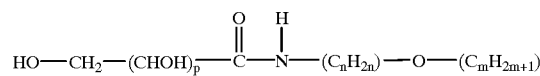

wherein p is a whole number from 1 to about 4; and $C_nH_{2n}$ is a straight or branched chain alkyl bridge in which n is a whole number of 1 to about 6, and is preferably 3; $C_mH_{2m+1}$ is a straight chain alky group in which m is a whole number of 1 to about 6 carbon atoms, and is preferably methyl. Most preferred is the above compound wherein p is 4, n is 3 and m is 1, which is methoxypropylgluconamide.

Suitable diamides include those of the general formula:

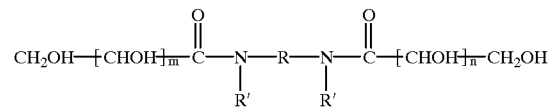

wherein m and n are each independently whole numbers from 0 to 4, and R is a substituted or unsubstituted hydrocarbon selected from the group consisting of aryl and alkyl radicals containing from about 2 to about 14 carbon atoms and each R' is independently hydrogen or $C_{1-4}$ alkyl.

4. Other Exfoliating Agents or Anti-Acne Actives

Other exfoliating agents, which are also known as anti-acne actives include benzoyl peroxide, resorcinol, and the like. Also suitable are benzoic acid derivatives, including those having the formula set forth below:

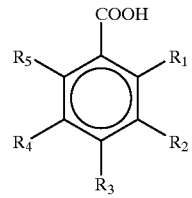

wherein $R_1$ is H, and $R_2$ through $R_5$ are each independently H, or OH with the proviso that there is at least one OH radical present.

Emollients

It may be desireable to include one or more emollients, or, for example, an emollient that is an organic ester, in the composition. Suggested ranges are 0.1–80%, preferably 0.5–75%, more preferably 1–60% by weight of the total composition. Suitable esters are, for example, sorbitan ester. In addition to those, other esters are also suitable as the nonaqueous nonpolar organic solvent. In general such esters have the formula RCO—OR' wherein each R and R' is independently a $C_{1-25}$ straight or branched chain saturated or unsaturated alkyl, alkylcarbonyloxyalkyl, alkoxycarbonylalkyl, aryl, which may be substituted or unsubstituted with halogen, hydroxyl, alkyl, and the like, in which the ester contains at least about six carbon atoms.

Examples of suitable esters include alkyl acetates (e.g. cetyl acetate, stearyl acetate), alkyl behenates, alkyl lactates, alkyl benzoates, alkyl octanoates, alkyl salicylates, and in particular $C_{12-15}$ alkyl benzoate. Examples of further esters are set forth on pages 502–506 of the CTFA Cosmetic Ingredient Handbook, Second Edition, 1992, which is hereby incorporated by reference.

Also suitable as emollients are silicones. It may be desireable to incorporate one or more silicones into the composition. Suggested ranges are 0.01–25%, preferably 0.1–20%, more preferably 0.5–15% by weight of the total composition. The silicones may be volatile or non-volatile. The term "volatile" means that the silicone has a measureable vapor pressure, i.e. a vapor pressure of at least 2 mm. of mercury at 20° C. If volatile, the silicone generally will have a viscosity of 0.5 to 25 centistokes at 25° C. Suitable volatile silicones include cyclic silicones, linear silicones, or mixtures thereof. Cyclic silicones (or cyclomethicones) are of the general formula:

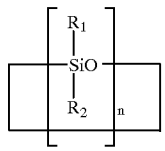

wherein n=3–7, and $R_1$ and $R_2$ are each independently H, $C_{1-8}$ alkyl, aryl, aralkyl, alkenyl, or a cylic or alicylic ring. Preferably $R_1$ and $R_2$ are each independently H or $CH_3$. Most preferably $R_1$ and $R_2$ are each $CH_3$.

Linear volatile silicones in accordance with the invention have the general formula:

$$(CH_3)_3Si-O-[Si(CH_3)_2-O]_n-Si(CH_3)_3$$

where n=0–7, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

The silicone may also be nonvolatile, and in particular water insoluble nonvolatile silicones. The nonvolatile silicones particularly provide a more emollient effect. The term "nonvolatile" means that the silicone has a vapor pressure of less than 2 mm. of mercury at 20° C. A variety of silicones fit this definition including dimethicone, phenyl trimethicone, diphenyl dimethicone, methicone, hexadecyl methicone, stearoxydimethicone, stearyl dimethicone, cetyl dimethicone, and so on.

Other suitable emollients are fats and oils. Preferably these materials are liquids or semi-solids at room temperature. Suggested ranges are 0.01–20%, preferably 0.1–15%, more preferably 0.5–10% by weight of the total composition. These fats and oils are generally defined as glyceryl esters of fatty acids (triglycerides), as well as the synthetically prepared esters of glycerin and fatty acids having the following general formula:

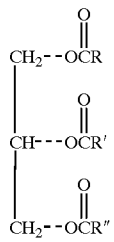

wherein R, R', and R" are each independently fatty acid radicals. Examples of such materials include oils such as apricot kernel oil, avocado oil, canola oil, olive oil, sesame oil, peanut oil, soybean oil, trilinolenin, trilinolein, trioctanoin, tristearin, triolein, sesame oil, rapeseed oil, sunflower seed oil, and so on.

It may be desireable to incorporate one or more silicone surfactants into the composition which exert a moisturizing or emollient effect on the skin. Suitable silicone surfactants used in the compositions of the invention may be liquid or solid at room temperature and are generally water-in-oil or oil-in-water type surfactants which are preferably nonionic, having an Hydrophile/Lipophile Balance (HLB) of 2 to 18. Preferably the organosiloxane is a nonionic surfactant having an HLB of 2 to 12, preferably 2 to 10, most preferably 4 to 6.

The silicone surfactant or emulsifier used in the compositions of the invention is a polymer containing a backbone with repeating siloxy units that may have cyclic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer.

In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer.

It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof The $C_{1-40}$alkyl may be non-interrupted, or interruped by one or more oxygen atoms, a benzene ring, amides, esters, or other functional groups.

Examples of other polymeric organosiloxane surfactants or emulsifiers include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane emulsifiers sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable. In addition, surfactants sold by Troy Corporation under the Troysol tradename, those sold by Taiwan Surfactant Co. under the tradename Ablusoft, those sold by Hoechst under the tradename Arkophob, are also suitable for use in the invention.

Preferrred silicone surfactants have the following formula:

$$CH_3-Si(CH_3)(CH_3)-O-\left[Si(CH_3)((CH_2)_p CH_3)-O\right]_x-\left[Si(CH_3)((CH_2)_3-O-PE)-O\right]_y-\left[Si(CH_3)(CH_3)-O\right]_z-Si(CH_3)(CH_3)-CH_3$$

wherein p is 0–40, and
PE is $(-C_2H_4O)_a(-C_3H_6O)_b-H$ where x, y, z, a, and b are such that the maximum molecular weight of the polymer ranges from 5,000 to approximately 50,000. Organosiloxane polymers that are surfactants useful in the compositions of the invention are commercially available from Goldschmidt Corporation under the ABIL tradename.

Another type of preferred organosiloxane emulsifier suitable for use in the compositions of the invention are emulsifiers sold by Union Carbide under the Silwet™ trademark. These emulsifiers have the formula set forth above wherein x is 0, z is 0, and y is 1.

Humectants

It may also be desireable to add one or more humectants to the compositions of the invention. Humectants will attract moisture to the composition and prevent it from becoming too dry on the laminate. In addition, humectants will assist in solvent activation of the composition upon contact with the solvent. Preferably the compositions contain 0.01–20%, more preferably 0.05–15%, most preferably 0.1–10% by weight of the total composition of humectant. The humectant acts as a skin conditioning agent and in addition may plasticize the polymer. Suitable humectants are:

1. Polyols

For purposes of this specification, polyols are defined as compounds which contain three or more hydroxyl groups per molecule. Examples of suitable polyols include fructose, glucamine, glucose, glucose glutamate, glucuronic acid, glycerin, 1,2,6-hexanetriol, hydroxystearyl methylglucamine, inositol, lactose, malitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mixtures thereof. An especially preferred polyol is glycerin.

2. Polymeric or Monomeric Ethers

Also suitable as humectants are homopolymeric or block copolymeric liquid ethers. Polymeric ethers are preferably formed by polymerization of monomeric alkylene oxides, generally ethylene or propylene oxides. Preferred monomeric ethers are those exhibiting the structure below were n=1. Preferred polymeric ethers exhibit the general structure below wherein n=2 to 20:

$$H-\left[OCH_2CH(R)\right]_n-OH$$

where R is H or $C_{1-10}$ straight or branched chain alkyl, and n is 1 to 20. Examples of such polymeric ethers include PEG, PPG, and derivatives thereof.

Other examples of suitable polymeric ethers include polyoxypropylene polyoxyethylene block copolymers having the general formula:

$$OH-\left[CHCH_2O(CH_3)\right]_x-(CH_2CH_2O)_y-\left[CHCHO(CH_3)\right]_z-H$$

wherein x is 1–200, y is 1–200 and z is 1–200. Such compounds are sold under the CTFA name Meroxapol 105, 108, 171, 172, 174, 178, 251, 252, 254, 255, 258, 311, 312, and 314.

3. Mono- and Dihydric Alcohols

Also suitable for use as humectants are mono- and dihydric alcohols of the general formula $R(OH)_n$ where n is 1 or 2 and R is a substituted or unsubstituted saturated $C_{2-10}$, preferably $C_{2-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, triethylene glycol, dipropylene glycol, and mixtures thereof.

4. Sorbitan Derivatives

Sorbitan derivatives, which are defined as ethers or esters of sorbitan, are also suitable humectants. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

Vitamins and Antioxidants

The compositions used in the method of the invention may contain vitamins and/or coenzymes, as well as antioxidants for skin conditioning and treatment. If so, 0.001–10%, preferably 0.01–8%, more preferably 0.05–5% by weight of the total composition are suggested. Suitable vitamins include ascorbic acid, the B vitamins such as thiamine, riboflavin, pyridoxin, and so on, as well as coenzymes such as thiamine pyrophoshate, flavin adenine dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof In addition, Vitamins D and K are suitable. Preferably the compositions of the invention contain 0.01–20%, more preferably 0.1–15%, more preferably 0.5–10% by weight of the total composition of ascorbic acid or derivatives thereof, such as esters or salts of ascorbic acid. Preferred is L-ascorbic acid, as well as esters of ascorbic acid such as ascorbyl palmitate, the the like.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

In addition to the skin conditioining agent, the composition may contain one or more additional ingredients.

Absorbents

The composition of the invention may contain 0.001–35%, preferably 0.01–20% more preferably 0.1–10%, by weight of the total composition, of absorbents, which aid in the absorption of oil or sebum from the skin surface. Preferably the absorbents have a particle size of 0.02 to 200, preferably 0.5 to 100, microns. Suitable absorbents include aluminum silicate, aluminum starch octenylsuccinate, amylodextrin, attapulgite, bentonite, calamine, calcium silicate, cellulose, chalk, colloidal oatmeal, corn flour, corn starch, cyclodextrin, dextrin, diatomaceous earth, dimethylimidazolidinone corn starch, fuller's earth, hectorite, hydrated silica, silica, kaolin, loess, magnesium aluminum silicate, magnesium carbonate, magnesium hydroxide, magnesium oxide, magnesium silicate, magnesium trisilicate, maltodextrin, microcrystalline cellulose, montmorillonite, oat bran, oat flour, oat meal, potato starch, talc, wheat powder, zeolite, and the like. Preferably the absorbent is silica or hydrated silica. The above mentioned absorbents may be surface treated with lecithin, amino acids, mineral oil, silicone oil or various other agents either alone or in combination, which coat the powder surface and render the particles more lipophilic in nature.

Pigments

The composition may contain various organic and inorganic pigments which provide coloration which may enhance consumer appeal as well as assist the absorbent in absorbing oil or sebum from the skin surface. Suggested ranges are 0.001–35%, preferably 0.01–20% more preferably 0.1–10%, by weight of the total composition. Suitable inorganic pigments include the iron oxides such as titanium dioxide, and other iron oxides, ultramarines, chromium, chromium hydroxide colors, and mixtures thereof. Suitable organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes.

The composition preferably contains a mixture of absorbent and pigment, in particular 0.1–20% absorbent and 0.1–20% pigment. More preferably the absorbent is silica and the pigment is titanium dioxide.

Sunscreens

The compositions of the invention may contain 0.001 –20%, preferably 0.01–10%, more preferably 0.05–8% of one or more sunscreens. The sunscreen may remain on the skin after application and removal of the laminate, and will assist in protecting the newly cleansed skin against UV radiation. A sunscreen is defined as an ingredient that absorbs at least 85 percent of the light in the UV range at wavelengths from 290 to 320 nanometers, but transmit UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on page 582 of the *CTFA Cosmetic Ingredient Handbook,* Second Edition, 1992, as well as U.S. Pat. No. 5,620,965, both of which are hereby incorpated by reference. Examples of such sunscreen materials are p-aminobenzoic acid (PABA), cinoxate, diethanolamine p-methoxycinnamate (DEA-methoxycinnamate), Digalloyl trioleate, dioxybenzone (Benzophenone-8), ethyl 4-[bis-(hydroxypropyl)]amnobenzoate (ethyl dihydroxypropyl PABA), 2-ethylhexyl-2-cyano-3,3-diphenylacrylate (octocrylene), ethylhexyl p-methoxycinnamate (Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), Padimate O, (Octyl Dimethyl PABA), 2-Phenylbenzimidazole-5-sulfonic acid (Phenylbenzimidazole Sulfonic acid), Red Petrolatum, Sulisobenzone (Benzophenone-4), triethanolamine salicylate (TEA-Salicylates), and so on.

Preservatives

The composition may contain 0.0001–8%, preferably 0.001–6%, more preferably 0.005–5% by weight of the total composition of one or more preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

The preferred compositions for use in the method of the invention contain:

5–75% nonionic polymer,

1–75% skin conditioning agent.

More preferably the skin conditioning agent is a beta hydroxy acid or derivatives, an N-alkoxyalkylamide, ascorbic acid, magnesium ascorbyl phosphate, vitamin E, dimethicone copolyol, glycerin, lecithin, green tea extract, or mixtures of these agents.

The Laminate

Figure 2:
FIG. 2 illustrates the laminate of the invention further comprising a third layer which is a thin synthetic film which is placed on top of the solvent activatable composition and acts as a release layer.
Figure 3:
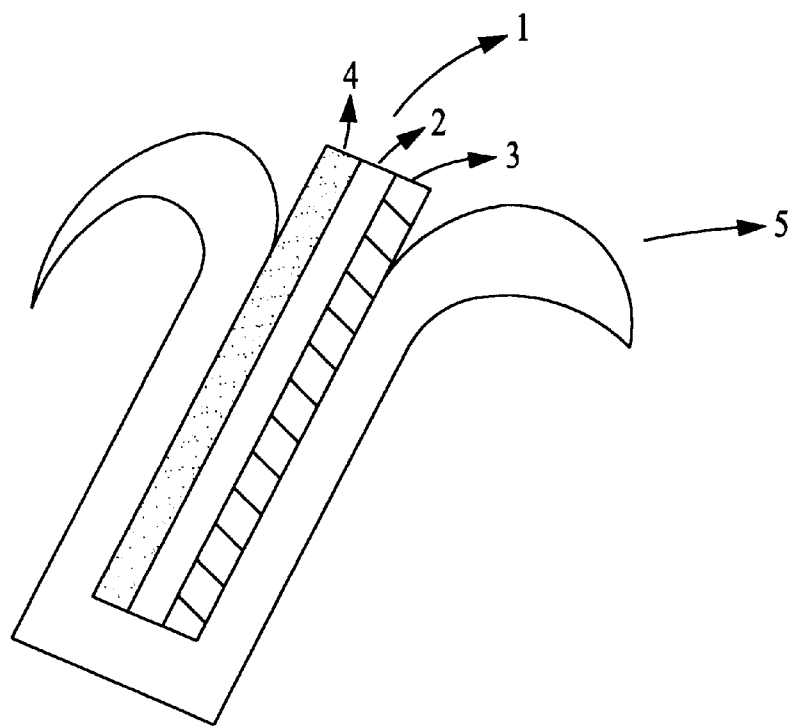
FIG. 3 illustrates the laminate of FIG. 2 enclosed in a hermetically sealed pouch which is partially cut away to permit viewing of the laminate in cross section.

The article or laminate used in the preferred embodiment of the invention is illustrated in FIGS. 1–3. FIG. 1 shows the laminate 1 which comprises a fabric strip 3 having the solvent activatable composition 2 layered thereon. FIG. 2 illustrates another laminate 1 used in the method of the invention where a protective release layer 4 covers the composition 2. The release layer 4 is removed by the consumer immediately prior to use. The laminate 1 is packaged in a hermetically sealed pouch 5, one embodiment of which is illustrated in FIG. 3, which shows an opened hermetically sealed pouch containing the laminate in cross-section. The hermetically sealed pouch prevents the composition impregnated into the strip from absorbing too much water from the atmosphere, thereby rendering the strip ineffective. Prior to use, the pouch 5 is torn open by the consumer and the laminate 1 removed. The release layer 4 is peeled off. The composition is activated by applying a thin layer of solvent to the composition 2, or to the skin (not shown) where the laminate will be applied.

The fabric strip 3 may be made from woven or non-woven fabrics having fibers which are hydrophilic, hydrophobic, or a combination of both. While the fabric is preferably a single layer, it may be a laminate of more than one layer, i.e. two hydrophobic layers, two hydrophilic layers, or a combination of hydrophobic and hydrophilic layers. Examples of hydrophobic fabrics include synthetic fibers such as polyester, polyethylene, polypropylene, polyurethane, nylon, hydrophobic rayon, and the like. Hydrophilic fibers include cotton, flax, wool, and cellulosic fibers such as cellulose acetate. Examples of laminates of hydrophobic and hydrophilic fabrics include those set forth in PCT International Application No. PCT/JP97/00631, published on Sep. 12, 1997, which is hereby incorporated by reference.

The fabric has sufficient porosity to permit evaporation of water or solvent when the laminate is applied to the skin.

Preferred are hydrophobic single layer non-woven fabrics made from synthetic fibers such as polyester, polypropylene, and hydrophobic rayon.

Figure 4A:
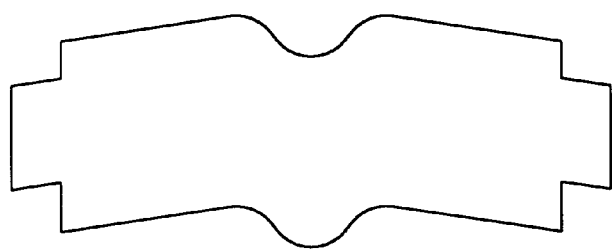
FIGS. 4a–4d illustrate various shapes for the laminate.
Figure 4B:
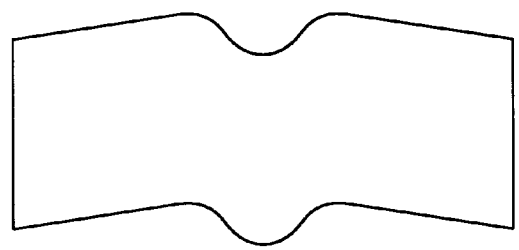
Figure 4C:
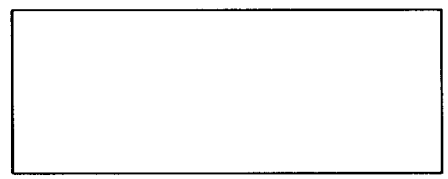
Figure 4D:
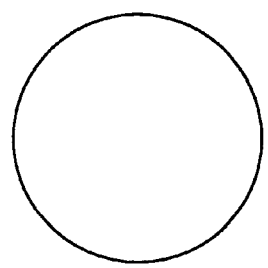

The release layer 4 may be made from a variety of synthetic film materials such as acetate, polyethylene, polyester, cellulose acetate and the like. Preferably the release layer 4 is made of a clear polyester film. It is desireable to have a release layer 4 because it better protects the composition 2 from the effects of humidity, moisture, and other types of damage. The laminate is preferably cut into an appropriate shape which facilitates its application to the desired area of the skin. The laminate and compositions of the invention may be used to clean all areas of facial or body skin, for example, nose, chin, forehead, cheeks, and the like. Examples of suitable shapes for the laminate are set forth in FIGS. 4a–4d. FIGS. 4a and 4b illustrate desireable laminate shapes for application to the nose area. FIGS. 4c and 4d illustrate examples of desireable shapes for application to the chin and cheeks. When designing suitable shapes the contours of skin and features are considered. For example, if the strip is to be used to clean the nose area, it is cut into a shape that facilitates easy application to the nose.

A variety of materials are suitable for making the pouch 5. It may be desireable to have a paper coated with synthetic polymeric material, or in the alternative, synthetic polymeric materials may be entirely used to make the pouch. The only requirement is that the pouch 5 should be substantially air-tight in order to protect the laminate from air and humidity.

The Method of The Invention

In the method of the invention, the laminate, composition side down is applied to the skin. At the time the laminate is applied to the skin, the composition layered thereon has been activated by contact with the appropriate solvent, which is preferably water. This may occur by wetting the skin and then applying the laminate, composition side down, to the wet skin, thereby activating the composition. In the alternative, a film of water may be spread across the composition and then the composition side of the laminate is applied to the skin. In some instances activation of the composition may simply occur because the skin surface is sufficiently moist, or the surrounding environment is sufficiently moist to cause the composition to become activated without application of the liquid. In such cases it is not then necessary to apply water to the skin or the laminate prior to application of the skin.

After the laminate is applied to the skin, it is left on the skin for a period of time sufficient to cause the solvent to substantially evaporate. The term "substantially evaporate" means that the solvent evaporates to a degree sufficient to cause the strip to remain adhered to the skin with sufficient adhesive strength to enable removal of dead surface skin cells, blackheads, and dirt and oil when the laminate is peeled off the skin. Preferably, the amount of time required for the solvent to evaporate to cause optimal cleaning activity ranges from about 5 to 45 minutes, preferably 5 to 20 minutes. When the laminate is peeled off, dirt, oil, dead surface cells, and blackheads remain adhered to the laminate and may be visible with the naked eye.

The method of the invention enables removal of dead surface cells, dirt, oil, and blackheads from the skin. Because the method helps clean the pores of the skin it is useful for preventing and/or ameliorating the effects of acne vulgaris and blemishes. In addition, by including one or more appropriate skin conditioning agents, the method of the invention can help reduce the appearance of fine lines and wrinkles on the skin, improve skin texture, even skin tone and pigmentation, and/or improve skin firmness and radiance. In addition, some of the pores of the skin can be reduced in size by continued practice of the method, due to consistent removal of blackheads, which enlarge pores.

To achieve the above effects it is recommended that the method of the invention be practiced at least once a week. Because the method of the invention is less harsh to skin it can be used more often.

The invention will be further described in connection with the following examples which are set forth for the purposes of illustration only.

EXAMPLE 1

A composition for use in the method of the invention was made according to the following formula:

|   |   | w/w % | |
|---|---|---|---|
|   |   | 1 | 2 |
| 1 | Diazolidinyl urea | 0.20 | 0.20 (preservative) |
| 1 | Disodium EDTA | 0.05 | 0.050 (preservative/chelator) |
| 1 | Methyl paraben | 0.10 | 0.10 (preservative) |
| 1 | Glycerin (96% aqueous solution) | 3.00 | 0.50 (skin conditioner) |
| 2 | Poly(N-vinylformamide)[1] | 35.00 | 20.00 (nonionic polymer) |
| 4 | Titanium dioxide | 1.50 | 0.50 (colorant) |
| 3 | Silica | 8.00 | 15.00 (absorbent) |
| 1 | Dimethicone copolyol | 0.50 | 0.50 (skin conditioner) |
| 1 | Lecithin | — | 0.20 (skin conditioner) |
| 5 | Salicylic acid/hydrolyzed vegetable protein complex (50:50) | 1.40 | 1.40 (skin conditioner) |
| 5 | Methoxypropylgluconamide (60% solution) | 0.10 | 0.10 (skin conditioner) |
| 5 | Magnesium ascorbyl phosphate | — | 0.001 (skin conditioner) |
| 5 | Green tea extract | — | 0.01 (skin conditioner) |
| 5 | Ascorbic acid | 0.10 | 0.01 (skin conditioner) |
| 5 | Vitamin E | — | 0.01 (skin conditioner) |
| 1 | Water | QS | QS |

[1]National Starch & Chemical, Bridgewater, New Jersey. A nonionic, water soluble fine white powder sold under the tradename Polymer 10174–02.

The composition was made by mixing the sequence 1 ingredients and heating to 70° C. until the solids dissolved. The mixture was cooled to 40 to 450° C. Sequence 2 was slowly added, using a prop mixer to ensure mixing. The sequence 3, 4, and 5 ingredients were then added and mixed well to ensure a homogeneity. Composition 1 had a viscosity of about 6,000 centipoise at 25° C. after 24 hours, when measured by Brookfield viscosity. Composition 2 had a viscosity of about 350 centipoise at 25° C.

EXAMPLE 2

Composition 1 from Example 1 was poured onto a 3 mil clear polyester film coated with an easy release silicone from Rexam (No. 10393). The fabric, a point bond non-woven rollstock thermal bond polyester having a nominal weight of 1.0 ounce per square yard, purchased from Wendell Textiles (No. PB-10), was applied on top of the composition with roller coating to form a laminate. The laminate was dried for 24 to 48 hours, and then cut into strips having the shape set forth in FIG. 4(a).

EXAMPLE 3

A skin cleansing composition suitable for use as a coating on the laminate, was made according to the following formula:

|  | w/w % |
| --- | --- |
| Water | QS to 100 |
| PVP[1] | 10.0 (nonionic polymer) |
| SDA 40B Alcohol | 25.0 (skin conditioner) |
| Methyl gluceth 20 | 15.0 (skin conditioner) |
| Salicylic acid/hydrolyzed vegetable protein (50:50) | 1.50 (skin conditioner) |
| Methoxypropylgluconamide | 0.1 (skin conditioner) |
| Magnesium ascorbyl phosphate | 0.01 (skin conditioner) |
| Tocopheryl acetate | 0.10 (skin conditioner) |
| Retinyl palmitate | 0.02 (skin conditioner) |
| Farnesyl acetate/farnesol/panthenyl triacetate | 1.0 (skin conditioner) |

[1]PVP K-120, International Specialty Products, polyvinylpyrrolidone having a molecular weight of 2,900,000 daltons.

The composition was made in the same manner as the composition in Example 1.

EXAMPLE 4

A skin cleaning composition suitable for coating the laminate was made according to the following formula:

|  | w/w % |
| --- | --- |
| Diazolidinyl urea | 0.20 (preservative) |
| Disodium EDTA | 0.05 (preservative/chelator) |
| Methyl paraben | 0.10 (preservative) |
| Glycerin | 4.50 (skin conditioner) |
| Poly N-vinyl formamide | 37.50 (nonionic polymer) |
| Titanium dioxide | 1.50 (colorant) |
| Silica | 12.00 (absorbant) |
| Dimethicone copolyol | 0.50 (skin conditioner) |
| Salicylic acid/hydrolyzed vegetable protein | 1.40 (skin conditioner) |
| Methoxypropylgluconamide | 0.10 (skin conditioner) |
| Ascorbic acid | 0.01 (skin conditioner) |
| Water | QS to 100 |

The above composition was made in the same way as the composition of Example 1.

EXAMPLE 5

Twenty one panelists (12 men and 9 women) exhibiting all skin types except dry and very dry, were asked to test the laminate prepared in Example 2 ("Test") versus a pore cleansing strip sold by Andrew Jergens company under the tradename "Bioré". The test products were coded. Panelists were asked to wet their nose thoroughly, peel the release layer off the laminate, and position one laminate, smooth side down, pressing the laminate to ensure good contact, on one side of the nose. The second laminate was applied in similar fashion to the other side of the nose. Panelists were instructed to let the laminates dry for 15 minutes, then slowly peel the laminates from the skin. They were then asked to rate the following attributes:

|  | (# panelists who agreed) | | |
| --- | --- | --- | --- |
|  | Biore | Test | No Preference |
| Which laminate has more accumulated (dirt, hairs, oil)? | 7 | 11 | 3 |
| Which laminate adhered more to the skin? | 8 | 10 | 3 |
| Did laminate feel comfortable when removed from nose? | 10 | 4 | 7 |
| Which pad do you prefer? | 8 | 10 | 3 |

The ingredients in the Bioré pore strip, from the labeling set forth on the package, are reproduced below:

Polyquaternium-37, silica, water, glycerin, dimethicone copolyol, titanium dioxide, methyl paraben.

EXAMPLE 6

Ninety panelists (33 men and 57 women) ranging in age from 18 to 55 and exhibiting all skin types, were asked to test the laminate prepared in Example 2 ("Test") versus a pore cleansing strip sold by Andrew Jergens company under the tradename "Bioré". The Test laminates were prepared by varying the amount of composition in the laminate as set forth below:

Test A: 3.3 oz. composition/square yard
Test C: 3.1 oz. composition/square yard
Test D: 3.8 oz. composition/square yard
Test B: Bioré nose strip Panelists were asked to wash their face with the cleanser provided and keep the nose area wet. The Test A, B, C, and D, nose strips were cut in half. The ninety panelists were broken up into three groups of thirty panelists. Panelists from each of the three groups were asked to apply a Test A, C, or D nose strip to one half of the nose and Test D nose strip to the other half of the nose. After 15 minutes, the panelists removed the nose strips from both sides of the nose with slow peeling. They were then asked to rate the following attributes:

|  | (# panelists who agreed) | | |
| --- | --- | --- | --- |
|  | Test A | Test B | No Preference |
| Test A vs. Test B (n = 30) |  |  |  |
| Which strip do you prefer for adhering to skin | 18 | 6 | 6 |
| Which strip do you prefer for blackhead, dirt, hair, and oil removal (as seen on pad) | 18 | 7 | 5 |
| Which pad do you prefer for not leaving a residue on your nose after removal | 4 | 15 | 11 |
| Which pad do you prefer overall | 14 | 9 | 7 |

-continued

|  | (# panelists who agreed) | | |
|---|---|---|---|
|  | Test C | Test B | No Preference |
| Test C vs. Test B (n = 30) | | | |
| Which strip do you prefer for adhering to skin | 12 | 13 | 5 |
| Which strip do you prefer for blackhead, dirt, hair, and oil removal (as seen on pad) | 12 | 12 | 6 |
| Which pad do you prefer for not leaving a residue on your nose after removal | 6 | 16 | 8 |
| Which pad do you prefer overall | 9 | 14 | 7 |

|  | (# panelists who agreed) | | |
|---|---|---|---|
|  | Test C | Test B | No Preference |
| Test D vs. Test B (n = 30) | | | |
| Which strip do you prefer for adhering to skin | 13 | 15 | 2 |
| Which strip do you prefer for blackhead, dirt, hair, and oil removal (as seen on pad) | 12 | 12 | 6 |
| Which pad do you prefer for not leaving a residue on your nose after removal | 4 | 19 | 7 |
| Which pad do you prefer overall | 14 | 15 | 1 |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for removing dead surface cells, dirt, oil, or blackheads from the skin comprising the steps of:
   (a) applying to the skin a laminate comprised of (i) a fabric strip, and (ii) a solvent activated composition containing at least one nonionic polymer comprising polymerized ethylenically unsaturated monomer units having the following formula:

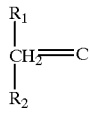

wherein:
      $R_1$ is hydrogen; $C_{1-30}$ straight or branched chain alkyl; or halogen;
      $R_2$ is NXCYO wherein X and Y are each independently hydrogen, or a $C_{1-30}$ straight or branched chain alkyl; in combination with at least one skin conditioning agent, composition side down,
   (b) leaving the laminate on the skin until the solvent has substantially evaporated,
   (c) peeling the laminate off the skin, thereby removing dead surface cells, dirt, oil, or blackheads from the skin.

2. The method of claim 1 wherein the solvent is water.
3. The method of claim 2 wherein the solvent activated composition is activated by moistening the skin with water prior to applying the laminate to the skin.
4. The method of claim 2 wherein the solvent activated composition is activated by moistening the composition with water prior to applying the laminate to the skin.
5. The method of claim 1 wherein the fabric strip is a single layer hydrophobic woven or non-woven fabric.
6. The method of claim 5 wherein the fabric strip is a hydrophobic single layer non-woven fabric.
7. The method of claim 6 wherein the fabric strip is a hydrophobic single layer non-woven fabric comprising polypropylene.
8. The method of claim 6 wherein the fabric strip is a hydrophobic single layer non-woven fabric comprising a blend of polypropylene and rayon.
9. The method of claim 1 wherein $R_1$ is hydrogen or methyl; and $R_2$ is NXCYO wherein X and Y are hydrogen.
10. The method of claim 9 wherein $R_1$ is hydrogen and $R_2$ is NXCYO wherein X and Y are hydrogen.
11. The method of claim 10 wherein the nonionic polymer is polyvinylformamide.
12. The method of claim 1 wherein the skin conditioning agent is an exfoliating agent.
13. The method of claim 12 wherein the exfoliating agent is an alpha or beta hydroxy acid or derivative thereof.
14. The method of claim 13 wherein the exfoliating agent is a beta hydroxy acid or derivative thereof.
15. The method of claim 14 wherein the beta hydroxy acid derivative is salicylic acid complexed to hydrolyzed vegetable protein.
16. The method of claim 1 wherein the skin conditioning agent is an ester.
17. The method of claim 1 wherein the skin conditioning agent is an N-alkoxyalkylamide.
18. An article for removing dead surface cells, dirt, oil, or blackheads from the skin comprising, in combination:
   a) a laminate comprised of (i) a fabric strip; and, layered onto said fabric strip, (ii) a solvent activatable composition comprised of at least one nonionic polymer comprising polymerized monomer units having the formula:

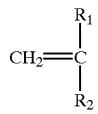

wherein:
      $R_1$ is hydrogen; $C_{1-30}$ straight or branched chain alkyl; or halogen;
      $R_2$ is NXCYO wherein X and Y are each independently hydrogen or a $C_{1-30}$ straight or branched chain alkyl; and at least one skin conditioning agent; and
   b) a hermetically sealed package in which said laminate is enclosed.

* * * * *